United States Patent [19]

De Simone et al.

[11] Patent Number: 4,670,616

[45] Date of Patent: Jun. 2, 1987

[54] AMS-1B CRYSTALLINE BOROSILICATE MOLECULAR SIEVE-BASED CATALYST COMPOSITIONS AND PROCESS FOR TOLUENE METHYLATION

[75] Inventors: Richard E. De Simone, Lisle; Muin S. Haddad, Naperville, both of Ill.

[73] Assignee: Amoco Corporation, Chicago, Ill.

[21] Appl. No.: 801,472

[22] Filed: Nov. 25, 1985

[51] Int. Cl.[4] .............................................. C07C 2/68
[52] U.S. Cl. .................................................... 585/467
[58] Field of Search ........................................ 585/467

[56] References Cited

U.S. PATENT DOCUMENTS 4,491,678  1/1985  Ods et al. ............................ 585/467

Primary Examiner—Curtis R. Davis
Attorney, Agent, or Firm—Reed F. Riley; William H. Magidson; Ralph C. Medhurst

[57] ABSTRACT

Described are catalyst compositions comprising a HAMS-1B crystalline borosilicate molecular sieve, the majority of the crystallites of which are between about 1 micron and about 15 micron in largest diameter, incorporated into an inorganic matrix, which have been impregnated with a small amount of a magnesium compound, said impregnated compositions having improved para-selectively for toluene methylation to xylene. Such impregnated compositions, when used for the methylation of toluene using methanol or dimethylether, yield a xylene product containing a very high proportion of the para isomer compared to corresponding unimpregnated or magnesium compound-impregnated borosilicate-based compositions containing standard size ($0.2\mu$ to $0.5\mu$) borosilicate molecular sieve crystallites.

8 Claims, No Drawings

AMS-1B CRYSTALLINE BOROSILICATE MOLECULAR SIEVE-BASED CATALYST COMPOSITIONS AND PROCESS FOR TOLUENE METHYLATION

BACKGROUND OF THE INVENTION

This invention relates to improved AMS-1B crystalline molecular sieve-based catalyst compositions, and particularly, to the use of such compositions having improved para-selectivity for toluene methylation. More particularly, it relates to improved compositions comprising larger crystallite AMS-1B molecular sieves incorporated into an inorganic matrix which have been impregnated by a magnesium compound and to processes for using these improved compositions to selectively para-methylate toluene to xylene.

In U.S. Pat. Nos. 4,504,690, 4,128,592, and 4,086,287 is taught modifying a ZSM-5 aluminosilicate zeolite catalyst with P, Mg, or P/Mg oxides to obtain high proportions of the 1,4-dialkyl isomer. Phosphorus or Mg modified ZSM-5 zeolite catalysts for the disproportionation of toluene are shown in J. Appl. Polym. Sci. 36, 209 (1981). Disproportionation of toluene to produce benzene over P, Mg modified crystalline aluminosilicate zeolite catalysts is described in U.S. Pat. No. 4,137,195. Alkylation or disproportionation of certain monosubstituted benzene compounds to achieve nearly 100% selectivty to para-disubstituted derivatives over magnesium compound-modified ZSM-5 aluminosilicate zeolite catalysts is reported in J. Am. Chem. Sec. 101, 6783 (1979). In the same article an increase in para-selectivity is shown by larger crystal size ZSM-5 zeolite catalysts during toluene methylation.

Use of Mg alone or in combination with P to modify a ZSM-5 aluminosilicate zeolite catalyst is described in U.S. Pat. No. 4,049,573 and the modified catalyst is used for converting alcohols and ethers to hydrocarbons. Again, Mg is used to modify ZSM-5 zeolite catalysts in U.S. Pat. No. 4,002,698 which can be used for selective production of p-xylene from charge stocks of toluene and a $C_3$–$C_{10}$ olefin; P modified catalysts for the methylation of toluene are also described.

Catalyst compositions, generally useful for hydrocarbon conversion, based upon AMS-1B crystalline borosilicate molecular sieve have been described in U.S. Pat. Nos. 4,268,420, 4,269,813, 4,285,919, and Published European application No. 68,796.

As described in the references in the paragraph above, catalyst compositions typically are formed by incorporating an AMS-1B crystalline borosilicate molecular sieve material into a matrix such as alumina, silica, or silica-alumina to produce a catalyst formulation. In one method of making AMS-1B crystalline borosilicate, sieve is formed by crystallizing sources for silicon oxide and boron oxide with sodium hydroxide and an organic compound. After crystallization, the resulting sodium form is ion exchanged with an ammonium compound and calcined to yield the hydrogen form of AMS-1B . In another and more preferred method, AMS-1B crystalline borosilicate is crystallized in the hydrogen form from a mixture containing a diamine in place of a metal hydroxide. AMS-1B borosilicates in hydrogen form are designated HAMS-1B . Typically, the hydrogen form sieve is gelled with an alumina sol, dried, and calcined to yield a catalyst composition.

SUMMARY OF THE INVENTION

Described herein are improved catalyst compositions comprising a HAMS-1B crystalline borosilicate molecular sieve, the majority of the crystallites of which are between about 1 micron and about 15 microns in largest dimension, incorporated into a matrix, which compositions have been impregnated with a small amount of a suitable magnesium compound and heated. Said impregnated compositions show an improved para-selectivity for toluene methylation to xylene when contacted under conversion conditions with methanol or methyl ether as compared with either unimpregnated borosilicate based compositions or magnesium impregnated compositions employing the standard size (0.2μ to 0.5μ) borosilicate sieve.

DETAILED DESCRIPTION OF THE INVENTION

The catalyst compositions used in this invention are based on AMS-1B crystalline borosilicate molecular sieve, which is described in U.S. Pat. Nos. 4,268,420; 4,269,813; and 4,285,919 and Published European Patent application No. 68,796, all incorporated herein by reference. AMS-1B crystalline borosilicate generally can be characterized by the X-ray pattern listed in Table A and by the composition formula:

$$0.9 \pm 0.2 \text{ } M_{2/n}O:B_2O_3:ySiO_2zH_2O$$

wherein M is at least one cation, n is the oxidation state of the cation, y is between 4 and about 600 and z is between 0 and about 160.

TABLE A

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

| | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 |

Wherein R is an organic compound and M is at least one cation having the oxidation state n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly and more preferably in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively and more preferably, AMS-1B crystalline borosilicate molecular sieve can be prepared by crystallizing a mixture of sources for an oxide of silicon, an oxide of boron, an alkylammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be about above about 0.05, typically below 5, preferably between about 0.1 and about 1.0, and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1, and most preferably about 0.02 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C., and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form, i.e., HAMS-1B. If the sieve was prepared using a metal hydroxide, such as sodium hydroxide, the hydrogen form typically, is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB, and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Examples of catalytically active elements include ruthenium, rhodium, iron, cobalt, and nickel. Mixtures of elements can be used. Other catalytic materials include ions and compounds of aluminum, lanthanum, molybdenum, tungsten, and noble metals such as ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, cobalt, iron, zinc, and cadmium. Specific combinations of nonnoble metals of Group VIII and other catalytic materials include ions or compounds of nickel and osmium, nickel and lanthanum, nickel and palladium, nickel and iridium, nickel and molybdenum, and nickel and tungsten.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. The optimum amount can be determined easily by routine experimentation.

The AMS-1B crystalline borosilicate useful in this invention is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt. % of the total composition. Catalytic compositions can contain about 0.1 wt. % to about 100 wt. % crystalline borosilicate material, and preferably contain about 10 wt. % to about 95 wt. % of such material, and most preferably contain about 20 wt. % to about 80 wt. % of such material.

The larger crystallite size borosilicate catalyst compositions impregnated with a magnesium compound according to this invention can be in powder form or already in extrudate form.

To make the larger crystallite size HAMS-1B crystalline borosilicate molecular sieves of this invention, attention must be given during the preparative process in solution to process variables. Slowing or stopping the agitation during reactant addition and digestion leads to larger sieve crystals, but the crystals are often too large, poorly formed and occlude impurities if made in this way. Thus, the agitation rate used in making the larger size crystallites is generally not changed or changed only slightly from that used in preparation of the standard size ($0.2\mu$ to $0.5\mu$) borosilicate sieve.

Temperature is an influential factor in crystallite size and increasing digestion temperature generally leads to larger crystallite size crystalline borosilicates. Increasing the template [e.g. $(Pr)_4NBr$] concentration generally also increases the crystallite size. The water/$SiO_2$ ratio can also be important and increasing the dilution of the solids in the growth broth also generally increases crystallite size.

In general, the process variables affecting crystallite size are the same as those already known in the chemical arts and can be relied upon by those skilled in the art to practice the invention herein.

The standard crystalline borosilicate molecular sieves already taught in the literature have a majority (greater than about 50 percent) of their crystallites in the range of about 0.2 micron to about 0.5 micron and are more or less spherical in shape. The larger crystallite size HAMS-1B borosilicates of use in this invention have a majority of their crystallites in the range of about one micron to about 15 microns. More preferably, the HAMS-1B borosilicates of this invention have a majority of their crystallites in the range of about 2 microns to about 10 microns and, most preferably, in the about 4 micron to about 6 micron range. Since the crystallites are three-dimensional, the crystallite size ranges given above refer to the longest dimension of the crystal. Crystallite sizes are conveniently measured using either optical microscopy or preferably, scanning electron microscopy by tabulating the number of crystallites in each size range over a small but representative sample of the borosilicate sieve using photomicrography.

To make an impregnated catalyst composition of this invention, a composition comprising the acid form of the crystalline borosilicate molecular sieve, the majority of the crystallites of which are between about 1 micron and about 15 microns, composited in an inorganic matrix is contacted with a magnesium compound-containing solution. The resulting mass is dried at temperatures up to about 150° C. driving off in this step essentially all of the impregnation solvent. The resulting composition is then activated by calcination for about 1 hour to about 24 hours at temperatures between about 300° C.

and about 800° C., more preferably, about 4 hours to about 24 hours at a temperature between about 400° C. and about 600° C.

The amount of magnesium incorporated with the catalyst composition should be from about 4% to 25% by weight, more preferably, from about 8% to about 15% by weight, percents calculated as percent magnesium. The incorporated magnesium is believed to be present substantially in the oxide form after heating.

Preferred magnesium compounds include most soluble magnesium salts, more preferably, magnesium nitrate or acetate is used.

The solutions of magnesium compounds used in impregnation may be made from polar or nonpolar solvents, including water and organic solvents generally. Solvents that are destructive of either the zeolite or matrix should be avoided. Water and alcohol are preferred solvents.

Methylation of toluene in the presence of the above-described catalyst compositions is effected by contact of the toluene with a methylating agent, preferably methanol or dimethyl ether, at a temperature between about 250° C. and about 700° C., and preferably between about 400° C. and about 600° C. The reaction can take place at atmospheric pressure, but the pressure may be within the approximate range of about 1 atmosphere to about 2000 psig. The molar ratio of methylating agent to toluene is generally between about 0.05 and about 5, preferably about 0.1 to about 1. When methanol is employed as the methylating agent a suitable molar ratio of methanol to toluene has been found to be approximately about 0.1-2 mols of methanol per mol of toluene. With the use of other methylating agents, such as acetaldehyde, dimethoxyethane, acetone, and methyl halides, the molar ratio of methylating agent to toluene may vary within the aforenoted range.

Reaction is suitably accomplished utilizing a weight hourly space velocity of between about 0.2 and about 500 and preferably between about 1 and about 100. The reaction product consisting almost 100% of para-xylene with small amounts of ortho- and meta-xylene together with unreacted toluene and methylating agent may be separated by any suitable means, such as fractional crystallization or distillation.

The following Examples will serve to illustrate certain specific embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

The reactions in the hydrocarbon conversion Examples below were carried out in a stainless steel reactor of plug-flow design. A 4:1 ratio of toluene to methanol was fed at 0.21 ml per minute into a preheater packed with inert Denstone packing and passed into a ½-inch O.D.×5-inch reactor tube filled with about a 5 g catalyst composition charge. The entire reactor and preheater assembly was supported in a fluidized sand bath maintained at reaction temperature. Product was collected in a cooled vessel as it dripped from the reactor and analyzed by gas chromatography on a 60 meter fused silica capillary column. All hydrocarbon isomer amounts are given in percents by weight. All magnesium contents are given in weight percent of the element.

EXAMPLE 1

Preparation of 1-2$\mu$ borosilicate molecular sieve was accomplished using 2000 g of water, 79 g of ethylenediamine, 102 g of boric acid, 27 g of tetrapropylammonium bromide, and 666 g of Ludox HS-40.

The above reactants were mixed with the aid of a homogenizer and then added to a 1-gallon autoclave whose impeller speed was set at 500 rpm. The temperature was set at 145° C. and the reaction mixture digested until high crystallinity molecular sieve was obtained ($\leq$4 days). The product was filtered, washed thoroughly with deionized water, dried at 130°-200° C. for 16 hours, and then calcined at 537° C. for 12 hours.

EXAMPLE 2

Preparation of 4-5$\mu$ borosilicate molecular sieve was accomplished by digesting a reaction mixture containing the following reactants: 2000 g of water, 79 g of ethylenediamine, 102 g of boric acid, 143 g of tetrapropylammonium bromide, and 666 g of Ludox HS-40.

The above reactants were mixed with the aid of a homogenizer and then digested at 165° C. in a 1-gallon autoclave whose impeller speed was set at 500 rpm. The crystalline product, isolated after 3.5 days of reaction was filtered, washed thoroughly with deionized water, dried at 130°-200° C. for 16 hours, and then calcined at 537° C. for 12 hours.

EXAMPLE 3

The preparation of 10-12$\mu$ borosilicate molecular sieve was carried out in a similar manner to Example 2 except that 176 g of ethylenediamine and 81 of tetrapropylammonium bromide were used. All other reagents and amounts were as described in Example 2.

EXAMPLES 4-6

The procedure for preparing catalyst compositions from Examples 1-3 sieves was identical. A 30 g portion of the sieve was placed in a blender with 45 Catapal ® SB alumina, which is $\alpha$-alumina hydrate, $\alpha$-Al$_2$O$_3$.H$_2$O. To this mixture was added 170 g of 5% acetic acid. The slurry was mixed at low speed for one minute, then poured into a crystallizing dish and placed into a drying oven at 130° C. As the liquid evaporated, the slurry was occasionally mixed. Drying was continued overnight, after which the sample was placed in a calcining oven brought up to 537° C. over a period of about 3 hours and held at this temperature overnight.

Examples 4, 5, and 6 catalyst compositions are made using 1-2$\mu$, 4-5$\mu$ and 10-12$\mu$ sieve respectively.

EXAMPLES 7-9

The magnesium compound impregnation step was the same for the catalyst compositions of Examples 4-6. A 9.0 g portion of catalyst composition was placed in a solution of 12.5 g of Mg(NO$_3$)$_2$.6H$_2$O dissolved in 25 ml of water. This mixture was placed in a heated shaker bath at 85°-90° C. and shaken for one hour. The heater was then turned off and the shaking continued for an additional 5 hours. Drying and calcination were carried out as described in Examples 4-6. Each impregnated catalyst composition, Examples 7-9, contain about 11.5 percent magnesium calculated as the element.

EXAMPLE 10-17

Methylation of toluene with methanol was carried out as set forth above under General using the unimpregnated catalyst compositions containing 1–2μ, 4–5μ, and 10–12μ sieves, Examples 4, 5, and 6. The data for these runs are tabulated in the Table below as Examples 12, 14, and 16. Examples 13, 15, and 17 in the Table are methylations carried out in the same way using methanol and the impregnated catalyst compositions of Examples 7, 8, and 9.

For additional comparison, a catalyst composition was made using the procedure of Examples 4–6 employing the standard crystal size borosilicate sieve (0.2–0.5μ). This composition was tested for its ability to alkylate toluene before (Example 10) and after (Example 11) impregnation. Impregnation of the composition was carried out as in Examples 7–9 and alkylation was carried out as is described under General above.

TABLE

Methylation of Toluene

| Example No. | Reax. T (°C.) | Conversion (%) | Selectivity o-xylene | Selectivity m-xylene | Selectivity p-xylene | X'tal Size (μ) | Mg Impregnated |
|---|---|---|---|---|---|---|---|
| 10 | 400 | 85 | 24.2 | 51.9 | 23.9 | 0.2–0.5 | No |
| 11 | 400 | 70 | 31.4 | 34.1 | 34.5 | 0.2–0.5 | Yes |
| 12 | 400 | 60 | 27.4 | 37.4 | 35.2 | 1–2 | No |
| 13 | 500 | 15 | <.05 | 3.9 | 96.1 | 1–2 | Yes |
| 14 | 400 | 30 | 19.5 | 27.3 | 53.2 | 4–5 | No |
| 15 | 500 | 15 | 5.8 | 9.0 | 85.2 | 4–5 | Yes |
| 16 | 400 | 35 | 15.3 | 17.5 | 67.2 | 10–12 | No |
| 17 | 500 | 15 | 4.0 | 5.5 | 90.5 | 10–12 | Yes |

What is claimed is:

1. A process for making paraxylene by methylating toluene in the presence of a catalyst composition comprising a HAMS-1B crystalline borosilicate molecular sieve, the majority of the crystallites of which are between about 1 micron and about 15 microns in largest dimesion, incorporated into an inorganic matrix, said composition impregnated by a magnesium compound and subsequently heated to substantially convert said compound to the oxide form.

2. A process for making paraxylene by methlating toluene in the presence of the catalyst composition of claim 1, said composition containing between about 4 and about 25% by weight magnesium.

3. A process for making paraxylene by methylating toluene in the presence of the catalyst composition of claim 2 wherein said HAMS-1B molecular sieve comprises from about 20 to about 80% incorporated into an alumina, silica, or silica-alumina matrix.

4. A process for making paraxylene by methylating toluene in the presence of the catalyst composition of claim 1 wherein the majority of the crystals of HAMS-1B molecular sieve are between about 2 microns and 10 microns.

5. A process for making paraxylene by methylating toluene in the presence of the catalyst composition of claim 4 wherein said composition contains between about 4 percent and about 25 percent by weight magnesium.

6. A process for making paraxylene by methylating toluene in the presence of the catalyst composition of claim 5 wherein said HAMS-1B molecular sieve comprises about 20 to 80% incorporated into an alumina, silica, or silica-alymina matrix.

7. A process for making paraxylene by methylating toluene with methanol in the presence of the catalyst composition of claim 3.

8. A process for making paraxylene by methylating toluene with methanol in the presence of the catalyst composition of claim 6.

* * * * *